United States Patent [19]

Kitaoka

[11] Patent Number: 5,342,342
[45] Date of Patent: Aug. 30, 1994

[54] DISPOSABLE DIAPERS

[75] Inventor: Hideaki Kitaoka, Funabashi, Japan

[73] Assignee: Uni-Charm Corporation, Ehime, Japan

[21] Appl. No.: 31,484

[22] Filed: Mar. 15, 1993

[30] Foreign Application Priority Data

Apr. 6, 1992 [JP] Japan .................. 4-084050

[51] Int. Cl.$^5$ .............................................. A61F 13/15
[52] U.S. Cl. ................. 604/385.2; 604/385.1; 604/387
[58] Field of Search .............. 604/385.2, 385.1, 380, 604/382, 378–379, 387

[56] References Cited

U.S. PATENT DOCUMENTS

| 4,246,900 | 1/1981 | Schröder | 604/385.2 |
| 4,795,454 | 1/1989 | Dragoo | 604/378 |
| 4,909,803 | 3/1990 | Aziz et al. | 604/385.2 |
| 4,961,737 | 10/1990 | Orlando | 604/385.2 |
| 5,062,840 | 11/1991 | Holt et al. | 604/385.1 |
| 5,069,678 | 12/1991 | Yamamoto et al. | 604/358 |
| 5,114,420 | 5/1992 | Igaue et al. | 604/385.2 |
| 5,176,672 | 1/1993 | Bruemmer et al. | 604/385.1 |

FOREIGN PATENT DOCUMENTS

| 0359410 | 3/1990 | European Pat. Off. . | |
| 0376022 | 7/1990 | European Pat. Off. . | |
| 0459178 | 11/1991 | European Pat. Off. . | |
| 0508477 | 4/1992 | European Pat. Off. | 604/385.2 |
| 0486006 | 5/1992 | European Pat. Off. . | |
| 4018097 | 8/1991 | Fed. Rep. of Germany | 604/385.2 |
| 3186262 | 8/1991 | Japan | 604/385.2 |
| 3202057 | 9/1991 | Japan | 604/385.1 |
| 2255896 | 11/1992 | United Kingdom | 604/385.2 |

Primary Examiner—Randall L. Green
Assistant Examiner—Rob Clarke
Attorney, Agent, or Firm—Fred Philpitt

[57] ABSTRACT

A disposable diaper so improved that a pair of flaps 17 extend from the transversely opposite side edges of an opening 16 centrally formed in the uppermost sheet 14 and these flaps 17 are provided along their outer side edges with elastic members 19, respectively, so that excretion can be reliably guided by sloped side walls formed by the flaps 17 to the opening 16.

3 Claims, 2 Drawing Sheets

DISPOSABLE DIAPERS

BACKGROUND OF THE INVENTION

This invention relates to a disposable diaper used to absorb and hold excretion from human body.

Japanese Utility Model Application Disclosure Gazette No. 1974-120439 discloses a diaper cover having a topsheet formed at its central zone with an opening extending longer in the longitudinal direction of the topsheet than in the transverse direction thereof, wherein the opening is provided along its peripheral edge with a longitudinally stretchable elastic member so as to define a closed loop-shaped elastic line. Japanese Patent Application Disclosure Gazette No. 1986-41304 also discloses a disposable diaper having a topsheet formed at its central zone with an opening extending longer in the longitudinal direction than in the transverse direction of the topsheet, wherein the opening is provided along its laterally opposite side edges with elastic members, respectively.

With these diaper cover and diaper both having the openings, excretion flows through said opening into a pocket defined between said topsheet and another topsheet underlying the first-mentioned topsheet and is held therein.

However, the user of diapers not always has them on with said opening being properly positioned to cover the urinary organs and/or the anus, in other words, said opening sometimes may get out of proper position with respect to the urinary organs and/or the anus, with a result that not all of excretion flows through said opening and a portion of excretion spreads over the uppermost sheet. Thus, the effect expected by providing of the uppermost sheet in addition to the topsheet and forming this uppermost sheet with said opening is substantially lost and excretion spreading over the uppermost sheet comes in contact with the user's skin, causing skin disease and at least giving the user unpleasant feeling.

It is an object of the invention to provide a disposable diaper so improved that all of excretion reliably flows through said opening.

SUMMARY OF THE INVENTION

The object set forth above is achieved, according to the invention, by a disposable diaper comprising an integral laminate composed of a liquid-permeable first topsheet, a liquid-impermeable backsheet, a liquid absorbent core sandwiched between said first topsheet and said backsheet, and a liquid-resistant second topsheet lying over said first topsheet, wherein said second topsheet is formed substantially at its central zone with an opening extending longer in the longitudinal direction than in the transverse direction of the second topsheet; wherein said second topsheet is bonded along its outer periphery to said first topsheet; and wherein longitudinally elastic members are attached onto said second topsheet along the peripheral edge of said opening, characterized by that a pair of liquid-resistant flaps extend from the transversely opposite side edges of said opening, said flaps being provided at least along their outer side edges with elastic members, respectively, and the longitudinally opposite ends of respective said flaps are bonded to said second topsheet.

Preferably, said second topsheet is centrally provided with a longitudinal cut line extending over a desired length and said second topsheet is further provided at the longitudinally opposite ends of said longitudinal cut line with transverse cut lines, respectively, so that portions of said second topsheet defined by these cut lines may be folded outwardly to form respective said flaps.

Preferably, there are provided between the lower surfaces of respective said flaps and the top surface of said second topsheet with another pair of elastic members so as to extend along the respective folding lines of said flaps.

With the diaper of the invention constructed as has been described, said flaps upper- and outwardly rise from their inner side edges under contraction of the elastic members provided along their outer side edges to form sloped side walls opposed to each other just like the side walls of a hopper which are opposed to each other. Excretion is guided by these sloped side walls to said opening. Liquid portion of the excretion is absorbed through said first topsheet into said core while solid portion of the excretion is introduced into a pocket defined between said first topsheet and the second topsheet.

BRIEF DESCRIPTION OF THE DRAWINGS

The invention will be described by way of example in reference with the accompanying drawings, in which.

PREFERRED EMBODIMENTS OF THE INVENTION

Figure 1:
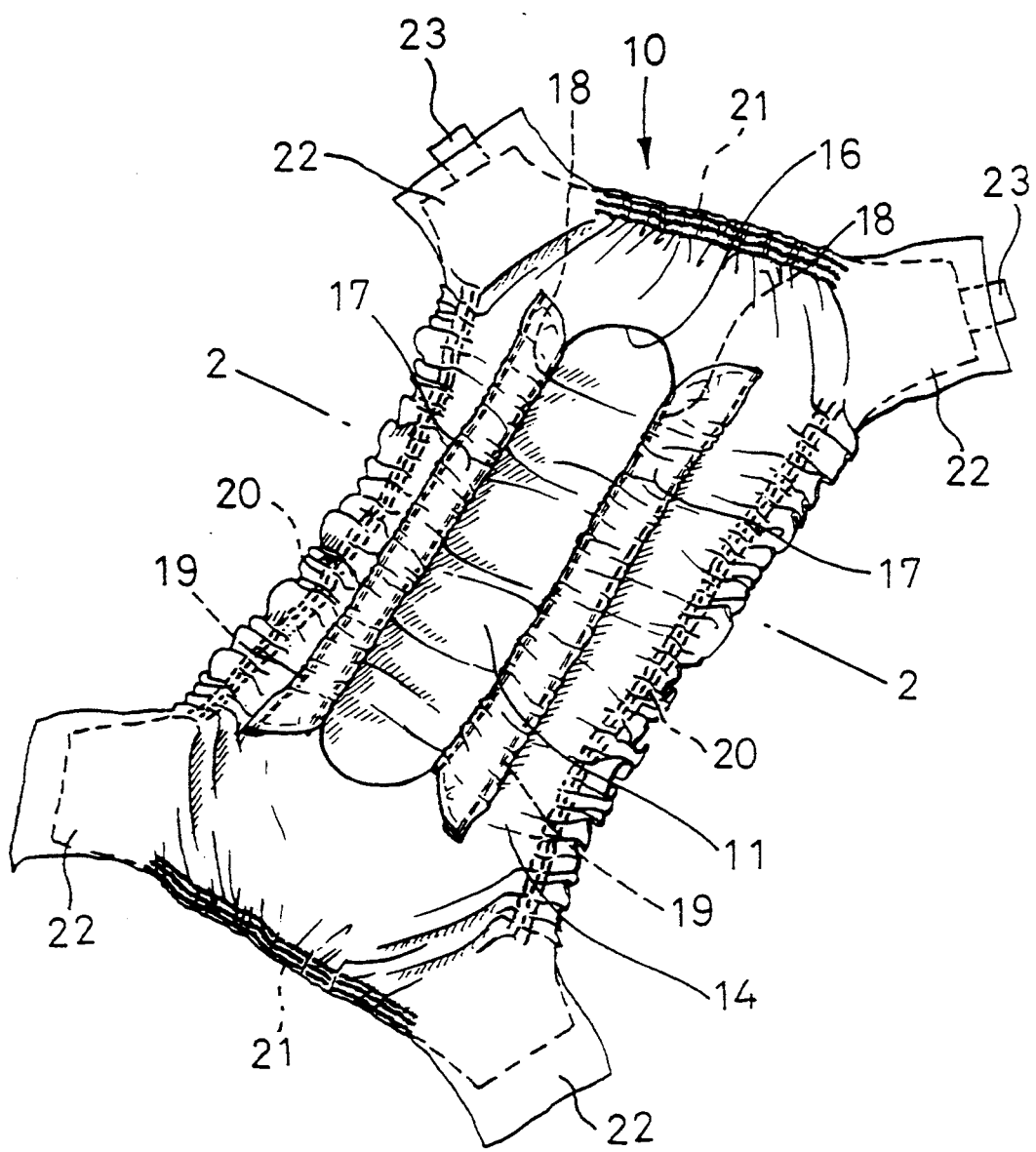
FIG. 1 is a perspective view showing the inner side of a disposable diaper constructed as an embodiment of the invention.
Figure 2:
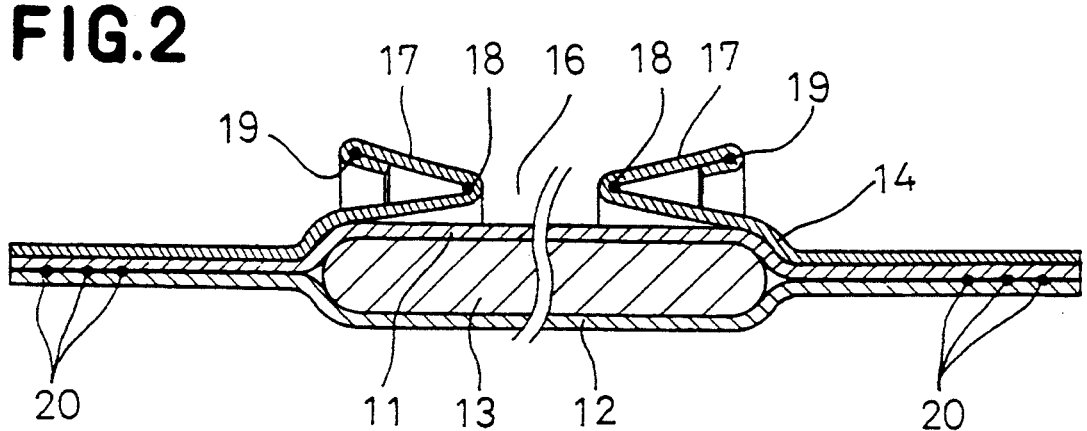
FIG. 2 is a sectional view showing this embodiment, in an enlarged scale, taken along a line 2—2 in FIG. 1.

Referring to FIGS. 1 and 2, a diaper 10 comprises an integral laminate 15 composed of a liquid-permeable first topsheet 11, a liquid-impermeable backsheet 12, a liquid-absorbent core 13 sandwiched therebetween, and a liquid-resistant second topsheet 14. The second topsheet 14 is centrally formed with an opening 16 which is longer in the longitudinal direction than in the transverse direction of this sheet 14 and has longitudinally opposite ends describing circular arcs, respectively. The opening 14 may be formed at least within the crotch zone.

Between the laterally opposite edges of the first topsheet 11 and the laterally opposite edges of the backsheet 12 both extending outward from both sides of the liquid-absorbent core 13, a plurality of elastic members 20 each comprising, in turn, a plurality of elastic rubber threads are attached, under their stretched states, with use of hot melt type adhesive (not shown), respectively, so as to be stretchable longitudinally of the sheets and fit tightly around the user's legs. Similarly, between the longitudinally opposite ends of the first topsheet 11 and the associated ends of the backsheet 12, there are provided a plurality of elastic members 21 each comprising, in turn, a plurality of elastic rubber threads, respectively, so as to be stretchable transversely of the sheets and fit tightly around the user's waist.

The first topsheet 11 may be made of nonwoven fabric, porous plastic film or the like, the backsheet 12 may be made of plastic film, laminated sheet of this plastic film and nonwoven fabric or the like, the liquid-absorbent core 13 may be made of a mixture of fluff pulp and high absorption polymer powder or the like. The second topsheet 14 and the flaps 17 are preferably made of water-repellent and highly air-permeable nonwoven fabric. It should be understood that, in description of the invention, the "liquid-resistant" material refers to the material having a sufficient degree of water-repellence to prevent liquid excretion from easily penetrating therethrough with the diaper being put on the user's body.

Referring to FIG. 1, the diaper 10 has two pairs of wing-like flaps 22 extending outward from the laterally opposite sides of the waist line, respectively, and the free ends of tape fasteners 23 attached to respective rear side wing-flaps 20 may be adhesively secured to the backsheet 12 to erect the diaper 10 around the user's body.

Now methods for forming the opening 16 in the second topsheet 14 and providing this opening 16 with the first and second elastic members 18, 19 will be described in reference with FIGS. 3 and 4.

Figure 3:
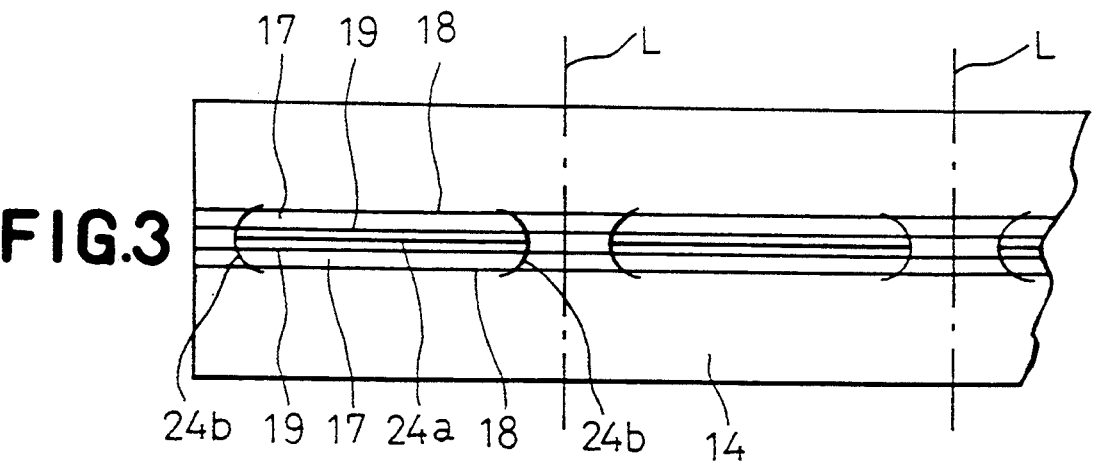
FIG. 3 is a plan view illustrating openings of a second topsheet as well as the first step in a method for attaching elastic members to the respective openings.

Referring to FIG. 3, a pair of continuous elastic members 19 spaced from each other in-parallel and another pair of elastic members 18 respectively outwardly spaced from the respective elastic members 19 also in parallel both being stretched by a predetermined elongation percentage are placed on the rear side of the second topsheet 14 along its central zone and simultaneously bonded thereonto with use of hot melt type adhesive. As will be apparent from FIG. 4, the second topsheet 14 is provided with a longitudinal straight cut line 24a extending intermediately of said pair of elastic members 19 substantially by a length of each individual diaper and with circular arc-shaped cut lines 24b extending transversely of said cut line 24a at the longitudinally opposite ends thereof to the respective elastic members 18 so as to form a pair of flaps 17. Edges extending along the cut line 24a are folded back to cover the respective elastic members 19 and the respective flaps 17 are folded outwardly along the respective elastic members 18 to form the opening 16. While maintaining the flaps 17 in a longitudinally stretched state, the longitudinally opposite ends of the flaps 17 are bonded to the second topsheet 14 by means of hot melt adhesive. Lengths of the elastic members 18, 19 longitudinally protruding from the respective cut lines 24b may be free from application of said adhesive and removed by suction means, for example, after said longitudinally opposite ends of the flaps 17 have been bonded to the second topsheet.

While the flaps 17 are preferably formed from the second topsheet 14 as in the embodiment shown, it is also possible to form these flaps 17 separately of the second topsheet 14 and then to connect them with the transversely opposite side edges of the opening 16.

Figure 4:
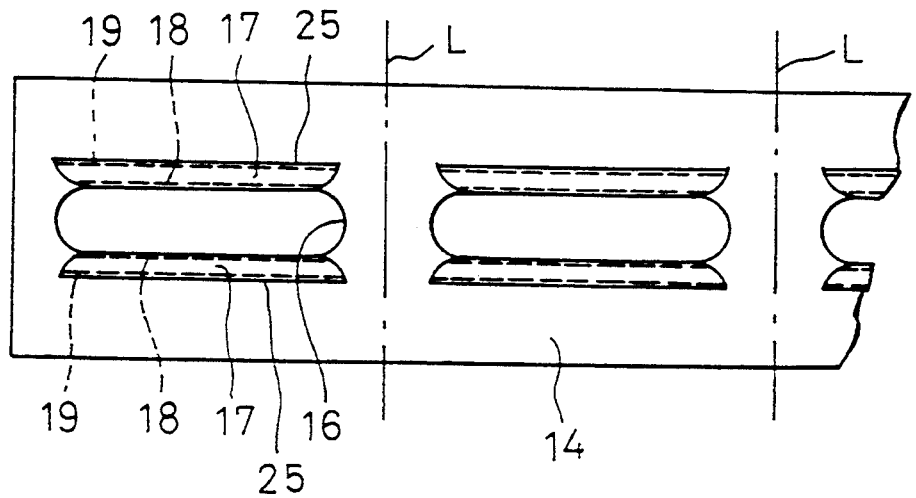
FIG. 4 is a plan view illustrating the openings of the second topsheet as well as the second step in the method for attaching the elastic members to the respective openings.

Referring to FIGS. 3 and 4, reference letter L designates an imaginary lines along which the second topsheet 14 is cut to obtain the individual diapers. This operation of cutting is effected by cutting the continuous laminate into the individual diapers after such continuous laminate has been constructed.

While the embodiment has been illustrated and described as so-called open type diaper utilizing the tape fasteners to close the waist line around the user's body, the invention will be applicable also to so-called pants type diaper (inclusive of training pants) having a continuous waist line.

With the diaper 10 being put on the user's body, as will be apparent from FIGS. 1 and 2, the opening 16 lifts out of the first topsheet 11 under contraction of the elastic members 18 and the flaps 17 are erected up- and outwardly along their inner side edges containing the elastic members 18 under contraction of the elastic members 19 so that these flaps 17 are opposed to each other to form the hopper-like sloped side walls. Excretion is guided by these sloped side walls to the opening 16. Liquid excretion is absorbed through the first topsheet 11 into the core 13 while solid excretion is introduced into a pocket defined between the first topsheet 11 and the second topsheet 14.

While it is preferred to provide the elastic members 18 along the side edges of the opening 16, these elastic members 18 are not essential to the invention because they have no significant contribution to formation of the sloped side walls by the flaps 17.

The diaper of this invention allows excretion to be reliably guided to the opening formed in the second topsheet without apprehension that excretion might partially spread over the area of the second topsheet extending outside the opening, which has been the most serious problem unsolved by the diaper of prior art, and additionally allows a size of the opening to be reduced.

What is claimed is:

1. A disposable diaper comprising:
   (a) a liquid-permeable first topsheet (11) having lateral sides, a liquid-permeable backsheet (12), and a liquid-absorbent core (13) sandwiched between said first topsheet (11) and said backsheet (12),
   (b) a liquid-resistant second topsheet (14) bonded along its outer periphery to said first topsheet (11), said second topsheet (14) having a central opening (16) that exposes a portion of said underlying topsheet (11), said openings (16) having spaced apart lateral sides and spaced apart end sections,
   (c) a pair of folded back flap members (17) extending outwardly from the lateral sides of said opening (16), each flap member (17) comprising a portion of said second topsheet (14) that is folded outwardly with respect to said opening (16) toward the lateral sides of said first topsheet (11) to thereby form a foldline, said flap member (17) having outer side edges and spaced apart end portions, said spaced apart end portions being bonded to said second topsheet (14) in areas of the second topsheet (14) which are spaced outwardly from said end sections of said opening (16),
   (d) a first elongated elastic member (19) in a stretched condition bonded to the outer side edge of each flap member (17) and to the portion of the second topsheet (14) beneath each flap member (17) so that said flap members (17) will lift away from said first topsheet (11) under contraction of said first elastic members (19) to thereby form a pocket above said first topsheet (11) and beneath said flap members (17), and
   (e) said flap members (17) forming spaced apart side walls that slope from the outer side edges of each flap member (17) downwardly to said central opening between said flap members (17).

2. A disposable diaper according to claim 1 wherein an elongated elastic member (18) in a stretched condition is bonded along each said fold line.

3. A disposable diaper comprising:
(a) a liquid-permeable first topsheet (11) having lateral sides, a liquid-permeable backsheet (12), and a liquid-absorbent core (13) sandwiched between said first topsheet (11) and said backsheet (12),
(b) a liquid-resistant second topsheet (14) bonded along its outer periphery to said first topsheet (11), said second topsheet (14) having a central opening (16) that exposes a portion of said underlying topsheet (11), said openings (16) having spaced apart lateral sides and spaced apart end sections,
(c) a pair of spaced apart flap members (17) that are both folded entirely outwardly toward the lateral sides of said topsheet (11) to thereby form spaced apart foldlines, each flap member (17) comprising a portion of said second topsheet (14), each flap member (17) having outer side edges and spaced apart end portions, said spaced apart end portions being bonded to said second topsheet (14) in areas of the second topsheet (14) which are spaced outwardly from said end sections of said openings (16),
(d) a first elongated elastic member (19) in a stretched condition bonded to the outer side edge of each flap member (17) and to the portion of the second topsheet (14) beneath each flap member (17) so that said flap members (17) will lift away from said first topsheet (11) under contraction of said first elastic members (19) to thereby form a pocket above said first topsheet (11) and beneath said flap members (17), and
(e) a second elongated elastic member (18) in a stretched condition is bonded along each said fold line.

\* \* \* \* \*